United States Patent [19]

Mitsumori et al.

[11] Patent Number: 4,950,667
[45] Date of Patent: Aug. 21, 1990

[54] PYRIDINYL ACETAMIDE COMPOUNDS USEFUL IN TREATING ULCERS

[75] Inventors: Naomichi Mitsumori, Kobe; Yasuhiro Nishimura, Fujiidera; Katsuhiro Ibata, Higashiosaka; Shiro Okuno, Osaka; Motoko Suzuki, Ibaraki, all of Japan

[73] Assignee: Hamari Chemicals, Ltd., Osaka, Japan

[21] Appl. No.: 394,565

[22] Filed: Aug. 16, 1989

[30] Foreign Application Priority Data

Aug. 22, 1988 [JP] Japan .................. 63-208544

[51] Int. Cl.$^5$ .............................................. A61K 31/44
[52] U.S. Cl. ..................... 514/227.8; 514/235.5; 514/252; 514/318; 514/352; 514/341; 514/342; 514/343; 544/60; 544/124; 544/360; 546/194; 546/276; 546/280; 546/281; 546/309
[58] Field of Search ............... 546/194, 276, 280, 309, 546/281; 44/60, 124, 360; 514/227.8, 235, 252, 318, 341, 352, 343

[56] References Cited

U.S. PATENT DOCUMENTS 4,297,357 10/1981 Miki et al. ....................... 546/309

Primary Examiner—John M. Ford
Assistant Examiner—Zinna Northington-Davis
Attorney, Agent, or Firm—Burgess, Ryan & Wayne

[57] ABSTRACT

There are provided acetamide compounds represented by the following formula;

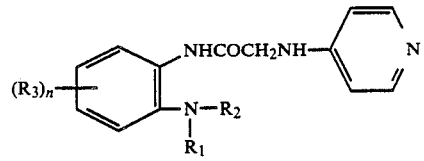

wherein $R_1$ and $R_2$ each independently represents a hydrogen atom, a $C_1$ to $C_6$ straight- or branched-chain alkyl or alkenyl group, a $C_3$ to $C_6$ cycloalkyl or cycloalkenyl group, or a $C_6$ to $C_{10}$ aromatic group; or $R_1$ and $R_2$ combine with each other in combination with the adjacent N and carbon atoms or further with at least one of nitrogen, oxygen and sulfur atoms to represent a 5- to 6-membered heterocyclic ring group; $R_3$ represents hydrogen atom, a $C_1$ to $C_6$ straight- or branched-chain alkyl or alkenyl group, a $C_3$ to $C_6$ cycloalkyl or cycloalkenyl group, a halogen atom, a $C_1$ to $C_6$ straight- or branched-chain alkyloxy group, or a $C_3$ to $C_6$ cycloalkyloxy or cycloalkenyloxy group; and n is an integer of 1 to 4, and their pharmaceutically acceptable salts.

The compounds and the salts exhibit potent anti-ulcer activity and are useful for treating ulcer in mammals.

5 Claims, No Drawings

PYRIDINYL ACETAMIDE COMPOUNDS USEFUL IN TREATING ULCERS

This invention relates to novel acetamide compounds and pharmaceutically acceptable salts thereof.

There have been found out a number of substances that are effective for the treatment of gastric ulcer and duodenal ulcer. As example of such substances, there may be mentioned cimetidine, gefarnate, omeprazole, etc. Nevertheless, these substances all suffer from disadvantages to be improved in terms of anti-ulcer activity or gastric-secretion suppressing activity. With a specific view to improving these disadvantages, development of new anti-ulcer drugs has been under way.

The present inventors have carried out intensive investigation in order to improve the conventionally known compounds, and as a result, found a group of substances having a new structure exhibits potent anti-ulcer activity, which led to the establishment of this invention.

This invention is directed to an acetamide compound represented by the formula [I] and a pharmaceutically acceptable salt thereof, and also directed to anti-ulcer agents containing the compound or the salt thereof as an active ingredient:

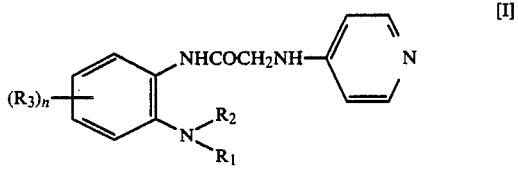

wherein $R_1$ and $R_2$ each independently represents a hydrogen atom, a $C_1$ to $C_6$ straight- or branched-chain alkyl or alkenyl group, a $C_3$ to $C_6$ cycloalkyl or cycloalkenyl group, or an $C_6$ to $C_{10}$ aromatic group; or $R_1$ and $R_2$ combine with each other in combination with the adjacent N and carbon atoms or further with at least one of nitrogen, oxygen and sulfur atoms to represent a 5- to 6-membered heterocyclic ring group; $R_3$ represents hydrogen atom, a $C_1$ to $C_6$ straight- or branched-chain alkyl or alkenyl group, a $C_3$ to $C_6$ cycloalkyl or cycloalkenyl group, a halogen atom, a $C_1$ to $C_6$ straight- or branched-chain alkyloxy group, or a $C_3$ to $C_6$ cycloalkyloxy or cycloalkenyloxy group; and n is an integer of 1 to 4.

Referring to the definitions of $R_1$ and $R_2$ in the formula [I], the $C_1$ to $C_6$ alkyl or $C_2$ to $C_6$ alkenyl group of straight or branched-chain group may be exemplified by methyl, ethyl, propyl, butyl, isopropyl, isobutyl, isopropenyl, 2-butenyl, hexenyl and the like; the $C_3$ to $C_6$ cycloalkyl or cycloalkenyl group may be exemplified by cyclopropyl, cyclohexyl, cyclopentyl, cyclopropenyl, cyclobutenyl, cyclohexenyl and the like; and the $C_6$ to $C_{10}$ aromatic group may be exemplified by substituted- or unsubstituted-phenyl or naphthyl group. As the substituents there may be exemplified straight- or branched-chain $C_1$ to $C_6$ alkyl or alkyloxy group, $C_2$ to $C_6$ alkenyl or alkenyloxy group, halogen, nitro group or the like. The aromatic group may be mono-, di- or tri-substituted by these substituents. The examples of the aromatic group are 4-methylphenyl, 4-fluorophenyl, 2-methoxyphenyl, 4-methoxyphenyl, 2-chloro-4-methoxyplenyl, 3,4,5-trimethoxyphenyl, 6-methoxynaphthyl, 2-methoxynaphthyl, 6-chloronaphthyl, 2-fluoronaphthyl, 2-bromo-6-methoxynaphthyl and the like.

As the 5-membered to 6-membered nitrogen-containing heterocyclic group wherein $R_1$ and $R_2$ combine with each other in combination with the adjacent N, or further with at least one of nitrogen, oxygen and sulfur atoms, there may be exemplified piperizino, piperazino, morpholino, thiomorpholino, thiazolyl, imidazolyl and the like.

In the definition of $R_3$, the $C_1$ to $C_6$ alkyl or $C_2$ to $C_6$ alkenyl group straight- or branched-chain, the $C_3$ to $C_6$ cycloalkyl or cycloalkenyl group, the halogen atom, the $C_1$ to $C_6$ straight- or branched-chain alkyloxy group, or the $C_3$ to $C_6$ cycloalkyoxy or cycloalkenyloxy group may be exemplified by the same examples as the respectively corresponding groups in $R_1$ and $R_2$. In case where n is an integer of not less than 2, a plurality of $R_3$ may be the same as or different from each other, as is exemplified in the above.

As the pharmaceutically acceptable salts of compound [I], there may be exemplified salts formed with organic acids, such as acetic acid, maleic acid, fumaric acid, tartaric acid, oxalic acid, methanesulfonic acid and p-toluenesufonic acid, etc.; inorganic acid such as hydrochloric acid, hydrobromic acid, sulfuric acid and phosphoric acid; acidic amino acids, such as glutamic acid, etc.; and the like.

The compound [I] of this invention can be produced, for example, by the steps of the reaction scheme as is illustrated in the following:

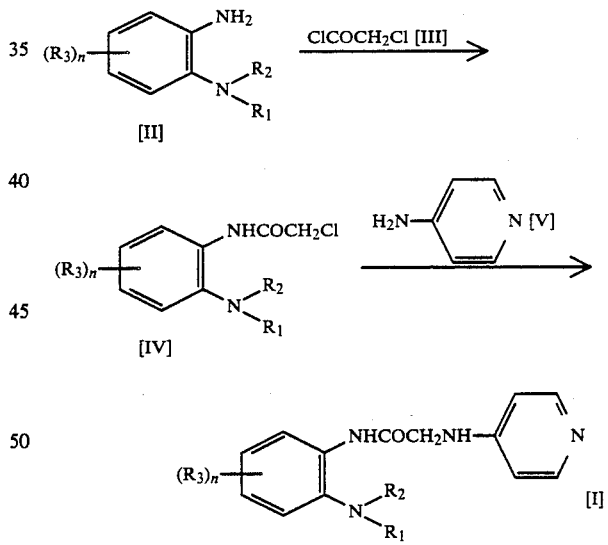

(wherein $R_1$, $R_2$, $R_3$ and n are as defined above)

The reaction of the compound [I] with chloroacetyl chloride [III] proceeds in an inert solvent, such as chloroform, tetrahydrofuran and toluene, in the presence of an organic base, such as triethylamine and pyridine, etc. or an inorganic base, such as anhydrous potassium carbonate, anhydrous potassium hydrogencarbonate, anhydrous sodium carbonate, anhydrous sodium hydrogencarbonate, etc. The reaction is carried out usually at a temperature up to refluxing temperature of the solvent employed, and preferably at a temperature between −10° C. to 30° C. By this procedure, the compound [IV] is formed.

Then, the compound [IV] is reacted with 4-aminopyridine [V] to give the compound [I].

This reaction is carried out in any indifferent solvent, such as methyl ethyl ketone, chloroform, dimethylformamide, isopropyl alcohol, etc. at a temperature from room temperature to 80° C.

For the purpose of removing hydrochloric acid evolved as the reaction proceeds, the reaction may be carried out in the presence of an inorganic base, such as anhydrous potassium carbonate, anhydrous potassium hydrogencarbonate anhydrous sodium carbonate, anhydrous sodium hydrogen-carbonate, potassium hydroxide, sodium hydroxide, etc., or an organic base, such as 1,8-diazabicyclo[5,4,0]-undecane, 1,5-diazabicyclo[4,3,0]nonane, 1,4-diazabicyclo[2,2,2]octane, etc. However, the reaction proceeds without addition of such base, whereby the objective compound [I] is obtained in the form of hydrochloride.

As the compound of this invention, there can be mentioned, for example, the following;

N-[2-(phenylamino)phenyl]-2-[(4-pyridinyl)amino]-acetamide,

N-[2-[(4-methylphenyl)amino]phenyl]-2-[4-pyridinyl)-amino]acetamide,

N-[2-[(4-fluorophenyl)amnio]phenyl]-2-[(4-pyridinyl)-amino]actamide,

N-[2-[(4-methoxyphenyl)amino]phenyl]-2-[(4-pyridinyl)-amino]acetamide,

N-[2-[(2-methoxyphenyl)amino]phenyl]-2-[(4-pyridinyl)-amino]acetamide,

N-[2-[(2-chlorophenyl)amino]phenyl]-2-[(4-pyridinyl)-amino]acetamide,

N-[2-[(phenylmethyl)amino]phenyl]-2-[(4-pyridinyl)-amino]acetamide,

N-[2-[[(4-methylphenyl)methyl]amino]phenyl]-2-[pyridinyl)-amino]acetamide,

N-[2-(imidazolin-1-yl)phenyl]-2-[(4-pyridinyl)-amino]acetamide,

N-[2-[(2,4-dimethoxyphenyl)amino]phenyl]-2-[(4pyridinyl)-amino]acetamide,

N-[2-[(3-hydroxy-4-methoxyphenyl)methylamino]-phenyl]-2-[(4-pyridinyl)amino]acetamide, N-[3-methoxy-2-[(4-methoxyphenyl)amino]phenyl]-2-[(4-pyridinyl)amino]actamide, N-[4,5-dimethoxy-2-(phenylamino)phenyl]-2-[(4-pyridinyl)amino]acetamide, N-[2-[(4-methoxyphenyl)amino]-3-methylphenyl]-2-[(4-pyridinyl)amino]acetamide, N-[3-fluoro-2-[(4-methoxyphenyl)amino]phenyl]-2-[(4-pyridinyl)amino]acetamide, N-[3-chloro-2-(phenylamino)phenyl]-2-[(4-pyridinyl)-amino]acetamide, N-[2-(morpholin-1-yl)phenyl]-2-[(4-pyridinyl)amino]-acetamide, 2-(4-pyridinyl)amino-N-[2-(thiomorpholin-1-yl)-phenyl]acetamide, 2-(4-pyridinyl)amino-N-[2-(pyrrol-1-yl)phenyl]-acetamide, N-[2-(piperidin-1-yl)phenyl]-2-[(4-pyridinyl)amino]-acetamide, N-[2-(isoindolin-1-yl)phenyl]-2-[(4-pyridinyl)amino]-acetamide, and the like.

The compounds as disclosed in this invention can be administered orally in the forms of tablets, capsules, granules and powders, and parenterally in the forms of injections and suppositories. The above pharmaceutical preparations may be incorporated with normally employed additives, such as auxiliary agents, stabilizers, wetting agents, emulsifying agents and buffer solutions, if necessary.

The compound of this invention are normally administered orally in a dose of 10 mg to 1 g per day, but the dosage amount can be varied according to the content of treatment and is not limited to the above range.

Described in the below are the examples and reference example to explain this invention further in detail, however, these examples are not understood to specify this invention.

REFERENCE EXAMPLE 1

Synthesis of 2-chloro-N-[2-(phenylamino)phenyl]-acetamide:

In 100 ml of chloroform, 10.4 g of N-phenyl-1,2-benzenediamine and 12.1 g of triethylamine were dissolved, and the mixture was cooled to −5° C. to 0° C., and then 13.6 g of chloroacetyl chloride was added dropwise thereto, holding the temperature of the mixture at not higher than 20° C. The reaction nearly went to completion when the addition was finished. After stirring for further 30 minutes, the reaction mixture was diluted with 50 ml of water. The organic layer was separated, washed with water, dried over anhydrous magnesium sulfate and then the solvent is evaporated under reduced pressure. The resulting solid was recrystallized from ethanol to give 15.6 g of crystals having a melting point of 112° C. to 113° C. Yield: 60.0%.

EXAMPLE 1

Synthesis of N-[2-(phenylamino),phenyl]-2-[(4-pyridinyl)-amino]actetamide hydrochloride:

In 75 ml of methyl ethyl ketone, 15.6 g of 2-chloro-N-[2-(phenylamino)phenyl]acetamide obtained in Reference Example 1 was added. After adding 5.64 g of 4-aminopyridine thereto, the mixture was heated at 80° C. under stirring, whereby crystals separated out according as the reaction proceeded. The reaction completed for 1 hour. The reaction mixture was stirred for further 2 hours, maintaining the temperature of the mixture at around 10° C., and the crystals separated out were collected by filtration to give 19.7 g of N-[2-(phenylamino)phenyl]-2-[4-pyridinyl)amino]acetamide hydrochloride. Yield: 92.5%.

IR (KBr, cm$^{-1}$): 3350, 1690, 1165, 1550, 1530, 1510.
NMR (DMSO-d$_6$, ppm): 5.19(br.s,2H), 6.64–7.40(m,10H), 7.50((m,1H), 8.04(m,3H), 8.32(br.,1H), 10.34(s,1H).

EXAMPLE 2

Synthesis of N-[2-[(4-methylphenyl)amino]phenyl]-2-[(4-pyridinyl)amino]acetamide hydrochloride:

2-Chloro-N-[2-[(4-methylphenyl)amino]phenyl-]acetamide which had been synthesized from N-(4-methylphenyl)-1,2-benzenediamine by substantially the same manner as described in Reference Example 1 and 4-aminopyridine were dissolved in chloroform and the solution was left on standing under stirring at room temperature overnight, whereby the reaction was completed. The resulting precipitates were collected by filtration and recrystallized from ethanol to give N-[2-[(4-methylphenyl)amino]phenyl]-2-[(4-pyridinyl-)amino]-acetamide hydrochloride.

Melting point, 232° C. to 238° C.

IR (KBr, cm$^{-1}$): 3350, 3240, 1685, 1665, 1600, 1545, 1510.

NMR (DMSO-d$_6$, ppm): 2.20(s,3H), 5.18(s,2H), 6.64-7.28(m,8H), 7.44(d,1H), 7.78(s,1H), 8.05(',2H), 8.30(br.,2H), 10.30(s,1H).

EXAMPLE 3

Synthesis of N-[2-[(4-fluorophenyl)amino]phenyl]-2-[(4-pyridinyl)amino]acetamide hydrochloride:

2-Chloro-N-[2-[(4-fluorophenyl)amino]phenyl]acetamide which had been synthesized from N-(4-fluorophenyl)-1,2-benzenediamine and chloroacetyl chloride by substantially the same manner as described in Reference example 1 and 4-aminopyridine were dissolved in N,N-dimethylformamide, and the solution was left on standing under stirring at room temperature overnight, whereby the reaction was completed. After the reaction mixture was left on standing under cooling at around 10° C., the resulting precipitates were collected by filtration and recrystallized from ethanol to give N-[2-[(4-fluorophenyl)amino]methyl]-2-[(4-pyridinyl)amino]acetamide hydrochloride.

Melting point, 239° C. to 246° C.

IR (KBr, cm$_{-1}$): 3345, 3240, 1685, 1665, 1605, 1595, 1550, 1525, 1500.

NMR (DMSO-d$_6$, ppm): 5.18(s,2H), 6.60-7.20(m,3H), 7.46(d,1H), 7.92(s,1H).

EXAMPLE 4

The compound of Example 1 was subjected to the determination of pharmacological activities by means of the procedure to be described in the below:

Water-immersion stress ulceration method

Male Slc:SD rats (7-weeks aged: divided in groups each consisting of 6 to 8 animals), after being fasted for 24 hours, were placed in stress cages and immersed in waters at 23° C. up to the xyphoid process, After stress loading for 7 hours, the rats were killed through exsanguination and the stomachs were removed, perfused in the inside with 10 ml of 2% formalin and then immersed in the same solution for 10 minutes for fixation. The stomachs were incised along the greater curvature, and the ulcers thus induced were measured for length under the stereoscopic microscope (magnification, ×10), whereby the total sum of the lengths was taken as an ulcer index (U.I., in mm). The test substance was given orally to rats in the form of a 4% gum arabic suspension 30 minutes before stress loading. The results are shown in Table 1.

Acute toxicity

A group of five male ddY mice (4-weeks aged) was used for testing.

The compound of Example 1 was suspended in 4% gum arabic solution to prepare a test pharmaceutical, which was given orally to each test animals once.

The test animals were observed for 7 days, and the LD$_{50}$ values were calculated to determine the acute toxicity The results are shown in Table 2.

TABLE 1

| Treatment | Dose mg/kg | Mean ± S.E. | Inhibition rate, % |
|---|---|---|---|
| Non-treated control | | 13.4 ± 2.71 | |
| Test substance | 10 | 13.0 ± 4.47 | 2.8 |
| | 30 | 3.8 ± 1.66 | 71.3* |
| | 100 | 1.5 ± 1.31 | 88.8** |

TABLE 1-continued

| Treatment | Dose mg/kg | Mean ± S.E. | Inhibition rate, % |
|---|---|---|---|
| Control reference*** | 30 | 5.2 ± 3.40 | 61.4 |

Note:
*p < 0.05;
**p < 0.01;
***Cimetidine

TABLE 2

| Test substance | LD$_{50}$ value |
|---|---|
| Compound of Example 1 | Not less than 2000 mg/kg |

As may be evident from the above toxicity test results, the compounds of this invention exhibit an extremely low degree of acute toxicity, and are adequately suitable for the use as a drug.

This invention can provide the novel acetamide compounds and also the means for the treatment of ulcers, such as gastric ulcer and duodenal ulcer, based on the use of the compounds.

We claim:

1. An acetamide compound of the formula:

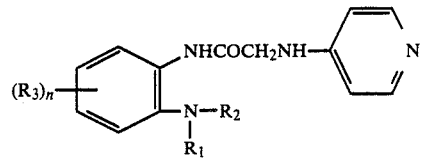

wherein R$_1$ and R$_2$ each independently represents hydrogen atom, a C$_1$-C$_6$ alkyl or C$_2$-C$_6$ alkenyl group of straight- or branched- chain, a C$_3$-C$_6$ cycloalkyl or cycloalkenyl group, or a C$_6$-C$_{10}$ aromatic group; or R$_1$ and R$_2$ when taken together with the nitrogen atom to which they are attached, present piperidinyl, piperazinyl, morpholinyl, thiomorpholinyl, thiazolyl, imidazolyl, pyrrolidinyl or pyrrolyl group; R$_3$ represents hydrogen atom, a C$_1$-C$_6$ alkyl or C$_2$-C$_6$ alkenyl group of straight- or branched chain, a C$_3$-C$_6$ cycloalkyl or cycloalkenyl group, a halogen atom, a C$_1$-C$_6$ straight- or branched-chain alkyloxy group, or a C$_3$-C$_6$ cycloalkyloxy or cycloalkenyloxy group; and n is an integer of 1 to 4; or a pharmaceutically acceptable salt thereof.

2. An acetamide compound of claim 1 wherein R$_1$ and R$_2$ each independently represents hydrogen atom, a C$_1$-C$_6$ alkyl or C$_2$-C$_6$ alkenyl group of straight- or branched-chain, a C$_3$-C$_6$ cycloalkyl or cycloalkenyl group, or a C$_6$-C$_{10}$ aromatic group; or R$_1$ and R$_2$ each independently represents a member selected from the group consisting of —CH$_2$—, —CH=CH$_2$—CH$_2$— and —CH=CH— or R$_1$ and R$_2$ when taken together with the nitrogen atom to which they are attached represent piperidinyl, piperazinyl, morpholinyl, thiomorpholinyl, thiazolyl, imidazolyl, pyrrolidinyl or pyrrolyl group; R$_3$ represents hydrogen atom, a C$_1$-C$_6$ alkyl or C$_2$-C$_6$ alkenyl group of straight- or branched-chain, a C$_3$-C$_6$ cycloalkyl or cycloalkenyl group, a halogen atom, a C$_1$-C$_6$ straight- or branched-chain alkyloxy group, or a C$_3$-C$_6$ cycloalkyloxy or cycloalkenyloxy group; and n is an integer of 1 to 4; or a pharmaceutically acceptable salt thereof.

3. A compound according to claim 2 wherein said heterocyclic ring group represented by the combination of R$_1$ with R$_2$ is piperidinyl, piperazinyl, morpholinyl, thiomorpholinyl, thiazolyl, imidazolyl, pyrrolidinyl or pyrrolyl group.

4. A pharmaceutical composition comprising a therapeutically effective amount of a compound according to claim 1 in association with a pharmaceutical carrier or diluent.

5. A method of treating ulcer in a mammal, which comprises administering a therapeutically effective amount of a compound according to claim 1 to a mammal in need of such treatment.

* * * * *